United States Patent [19]
Meinetsberger

[11] Patent Number: 5,037,973
[45] Date of Patent: Aug. 6, 1991

[54] BIS-ALDONAMIDES AND PROCESS FOR THEIR PREPARATION

[75] Inventor: Eike Meinetsberger, Munich, Fed. Rep. of Germany

[73] Assignee: Luitpold-Werk Chemisch-pharmazeutische Fabrik GmbH & Co., Munich, Fed. Rep. of Germany

[21] Appl. No.: 256,768

[22] Filed: Oct. 12, 1988

[30] Foreign Application Priority Data

Oct. 14, 1987 [DE] Fed. Rep. of Germany ....... 3734853

[51] Int. Cl.⁵ .................... C07H 15/04; C07H 15/18
[52] U.S. Cl. ...................................... 536/53; 536/1.1; 536/4.1; 536/54
[58] Field of Search ...................... 536/4.1, 1.1, 53, 54

[56] References Cited

U.S. PATENT DOCUMENTS 4,229,446 10/1980 Takemoto et al. .................. 514/159
4,357,326 11/1982 Nair et al. ........................... 536/118
4,587,250 5/1986 Klauser et al. ...................... 514/278

OTHER PUBLICATIONS

"Synthesis fo a New Class of Model Glycolipids" (Depo. Biol. Chem., Univ. of Michigan, Ann Arbor, MI) Carbohydr. Res. 19/8, 67(1), Cl–C3 A New Class of Nonionic Detergents with a Gluconamide Polar Group, (Lab. Vision Res., Natl. Eye Inst., Bethesda, MD) Anal. Biochem. 1983, 130(2), 485–90.
"Affects of Nonionic Contracts Media on the Components of Coagulation and and Complement Systems" (Med. Cent., Loyola Univ., Maywood, IL) Invest. Radiol. 1983, 18(3), 279–84.

Primary Examiner—Ronald W. Griffin
Attorney, Agent, or Firm—Burns, Doane, Swecker & Mathis

[57] ABSTRACT

The invention relates to bisaldonamides, in which the underlying aldonic acids can be linked glycosidically in the 3-, 4- or 6-position with a galactopyranosyl, mannopyransyl, glucopyranosyl or oligopyranosyl radical. They are starting products for the preparation of the corresponding polysulfuric acid esters.

13 Claims, No Drawings

BIS-ALDONAMIDES AND PROCESS FOR THEIR PREPARATION

DESCRIPTION

The invention relates to bis-aldonamides of the general formula I

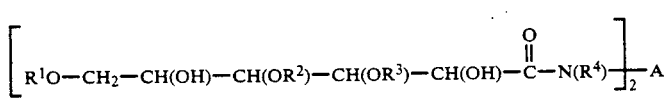
(I)

in which either all radicals $R^1$, $R^2$ and $R^3$ stand for a hydrogen atom, or two of the radicals $R^1$, $R^2$ and $R^3$ stand for a hydrogen atom and the third stands for a radical of the formulae II to VII,

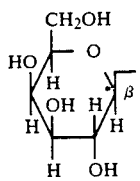
(II)

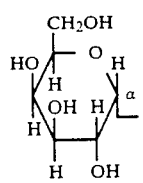
(III)

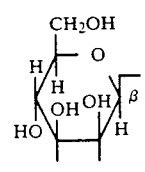
(IV)

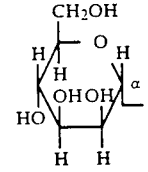
(V)

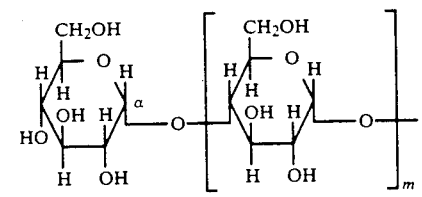
(VI)

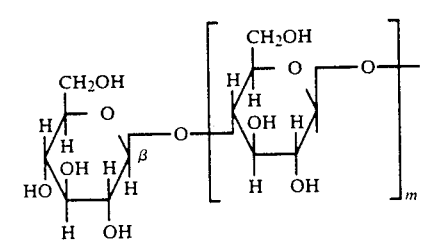
(VII)

m stands for 0, 1, 2, 3, 4, 5 or 6,

A in formula I stands for a straight-chain or branched, saturated alkylene radical having 2 to 22 carbon atoms which is optionally substituted by one or more radicals —$CO_2R^5$, and this alkylene radical is optionally interrupted by up to 5 —O—, —S—, —S—S—, —S(O)$_n$—,

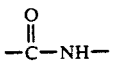

or/and —$NR^6$— groups or cycloalkylene or arylene radicals, or A stands for a single bond or the radical

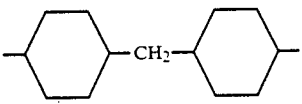

n is 1 or 2, $R^4$, $R^5$ and $R^6$ simultaneously or independently of one another denote a hydrogen atom or a $C_1$-$C_6$-alkyl radical, and their salts with inorganic or organic bases, with the proviso that in the case of bis-gluconic acid amides a) $R^1$, $R^2$, $R^3$ and $R^4$ do not simultaneously denote hydrogen atoms and that b) when $R^2$ is a radical of the formula II, and $R^1$, $R^3$ and $R^4$ are simultaneously hydrogen atoms, A is not —$(CH_2)_2$— in this case and that c) when $R^2$ is a radical of the formula VI, in which m=0, 1, 2, 3 or 5, and $R^1$, $R^3$ and $R^4$ are simultaneously hydrogen atoms and A is an unsubstituted, straight-chain alkylene radical, in this case the number of chain members is an uneven number.

The compounds according to the invention are useful intermediates. Highly valuable active compounds having surprising pharmacological properties are obtained from them by reaction with sulfating agents. Some bis-aldonamides are already known and for this reference is made to the following literature sources: F. Scholnick, P. E. Pfeffer, J. Dairy Sci 63 (3), 471 (1980); W. N. Emmerling, B. Pfannemüller, Starch 33 (6), 202 (1981); G. Ziegast, B. Pfannemüller, Makromol. Chem. 185, 1855 (1984); J. Masse et al., C. R. Acad. Sci., Ser. 3, 301 (1), 27 (1985); K. Dill et al., Inorg. Chim. Acta, 106 (4), 203 (1985). However, the known compounds are in no case described as intermediates for the preparation of the abovementioned active compounds. Emmerling and Pfannemüller used them in enzymatic syntheses of amylose chains using potato phosphorylase. Scholnick and Pfeffer and also K. Dill et al. studied their chelating properties and J. Masse et al. studied their influence on growth and chlorophyll content of cereals.

The following comments apply to the various substituents or radicals (in the various formulae indicated) mentioned in connection with the present invention:

The aldonic acids underlying the present bis-aldonamides possess the general formula X.

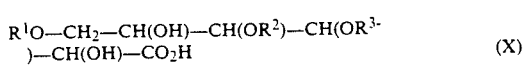
(X)

in which $R^1$, $R^2$ and $R^3$ possess the meaning indicated. These aldonic acids can be present in the D-form, the L-form or in the form of their racemates, preferably in their naturally predominant form.

Examples of these aldonic acids of the formula X comprise the hexonic acids allonic acid, altronic acid, galactonic acid, gluconic acid, gulonic acid, idonic acid, mannonic acid and talonic acid, preferably galactonic acid, gluconic acid, gulonic acid and mannonic acid. Further examples are derivatives of these hexonic acids which are connected glycosidically on the oxygen atoms in the 3-, 4- or 6-position with a radical of the formulae II to VII. The bond here can be α- or β-glycosidic. The radicals II to V are galactopyranosyl and mannopyranosyl radicals. The radicals VI and VII are glucopyranosyl radicals (in the case where m=0) and α(1→4)- or β(1→4)-linked oligoglucopyranosyl radicals (when m=1 to 6). Preferably, the index m in the formulae VI and VII stands for 0 or 1. The saccharide units linked with the aldonic acid are normally present in the D-form. Examples of hexonic acids of the general formula X which are substituted by radicals of the formulae II to VII are glucopyranosylgluconic acids, glucopyranosylmannonic acids, glucopyranosylgalactonic acids, galactopyranosylgluconic acids, mannopyranosylgluconic acids, mannopyranosylmannonic acids and oligoglucopyranosylgluconic acids. Lactobionic acid (4-O-β-D-galactopyranosylgluconic acid), gentiobionic acid, melibionic acid (6-O-α-D-galactopyranosylgluconic acid), mannobionic acid, cellobionic acid (4-O-β-D-glucopyranosylgluconic acid) and maltobionic acid (4-O-α-D-glucopyranosylgluconic acid) and also maltotrionic acid and cellotrionic acid are preferred here.

Examples of inorganic and organic salts are the ammonium, lithium, sodium, potassium, magnesium, calcium and aluminum salts and the salts with ethanolamine, triethanolamine, morpholine, pyridine and piperidine. The sodium, potassium, calcium, aluminum and ethanolamine salts are preferred.

Examples of the straight-chain or branched, saturated alkylene radicals having 2 to 22 carbon atoms representing the group A are ethylene, tri-, tetra-, penta-, hexa-, hepta-, octa-, nona-, deca-, undeca-, dodeca-, tetradeca-, hexadeca-, octadeca-, icosa- and docosamethylene and also methylethylene, methylpropylene, methylbutylene, methylpentylene and dimethylethylene. Ethylene, tri-, tetra-, hexa-, nona-, dodeca- and docosamethylene and also methylethylene and methylpentylene are preferred.

Examples of arylene radicals by which the alkylene radical of the group A can be interrupted are phenylene, naphthylene, anthrylene, phenanthrylene and fluorenylene. In this connection, ortho-, meta- and para-phenylene radicals are preferred.

Examples of cycloalkylene radicals by which the alkylene radical of the group A can be interrupted are cyclopentylene, cyclohexylene, cycloheptylene and cyclooctylene, 1,3- and 1,4-cyclohexylene being preferred here.

The straight-chain or branched, saturated alkylene radical of the group A preferably possesses 2 to 12 carbon atoms. If the straight-chain or branched, saturated alkylene radical of the group A is interrupted by one of the radicals or groups mentioned, it is preferably 1 or 2 of those radicals or groups.

Specific examples according to the definition which are alkylene radicals representing group A are groups derived from the following α, ω-diamines:

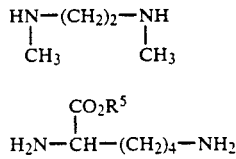

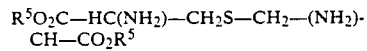

Enantiomers of lysine ($R^5$=H) and its esters ($R^5$=$C_1$-$C_6$-alkyl)

containing S atoms

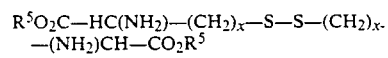

Diastereomers of lanthionine ($R^5$=H) and esters ($R^5$=$C_1$-$C_6$-alkyl)

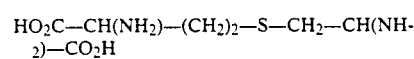

Diastereomers of cystine (x=1, $R^5$=H) and esters ($R^5$=$C_1$-$C_6$-alkyl)
Diastereomers of homocystine (x=2, $R^5$=H) and esters ($R^5$=$C_1$-$C_6$-alkyl)

$HO_2C-CH(NH_2)-(CH_2)_2-S-CH_2-CH(NH_2)-CO_2H$

Diastereomers of cystathionine containing NH groups

| containing NH groups: | |
|---|---|
| $H_2N(-CH_2-CH_2-NH)_x-CH_2-CH_2-NH_2$ | x = 1 diethylenetriamine |
| | x = 2 triethylenetetramine |
| | x = 3 tetraethylenepentamine |
| $H_2N-(CH_2)_2-NH-(CH_2)_3-NH-(CH_2)_2-NH_2$ | 1,9-diamino-3,7-diazanonane |
| $H_2N-(CH_2)_3-NH-(CH_2)_2-NH-(CH_2)_3-NH_2$ | 1,10-diamino-4,7-diazadecane |
| $H_2N-(CH_2)_6-NH-(CH_2)_6-NH_2$ | bis-(6-aminohexyl)amine |
| $H_2N-(CH_2)_3-NH-(CH_2)_4-NH-(CH_2)_3-NH_2$ | spermine |
| $H_2N-(CH_2)_4-NH-(CH_2)_3-NH_2$ | spermidine |
| $H_2N-(CH_2)_3-NH-(CH_2)_3-NH-(CH_2)_3-NH_2$ | 1,11-diamino-4,8-diazaundecane |
| containing O atoms: | |
| $H_2N-(CH_2)_2-O-(CH_2)_2-NH_2$ | bis-(2-aminoethyl) ether |

The group A can preferably stand for the following radicals:

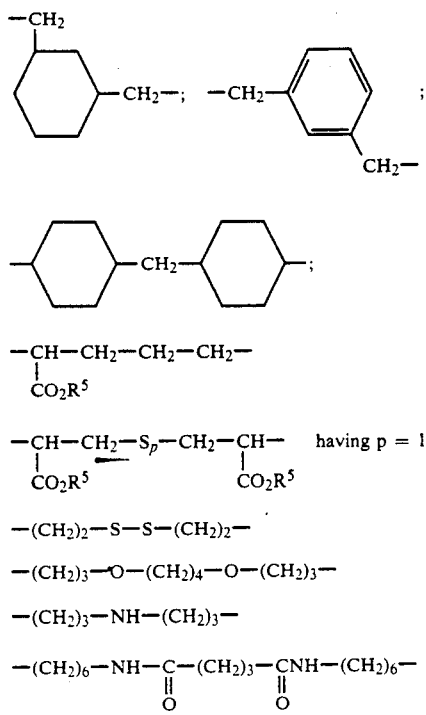

Examples of $C_1$-$C_6$-alkyl radicals of the groups $R^4$, $R^5$ and $R^6$ are methyl, ethyl, n-propyl, n-butyl, n-pentyl, n-hexyl, isopropyl, isobutyl, tert.-butyl, neo-pentyl, methyl, ethyl, n-propyl, isopropyl, tert.-butyl and n-butyl being preferred.

The invention also relates to a process for the preparation of the bis-aldonamides of the general formula I. In this connection, the lactones of the aldonic acids X are allowed to react in a solvent with a diamino compound of the general formula $R^4HN$—A—$NHR^4$, in which $R^4$ possesses the indicated meaning, in analogy to processes known from the literature (see preceding literature sources). The lactones can be employed both in the 1,5-lactone form of the general formula VIII and also in the 1,4-lactone form of the general formula IX.

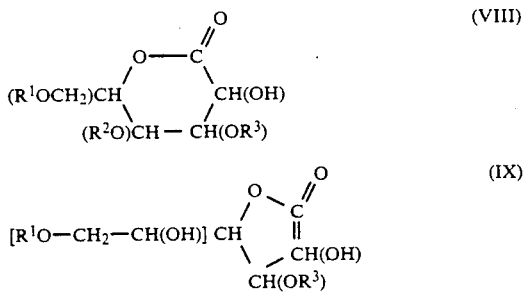

They are obtained by elimination of water from the aldonic acids X. The aldonic acids can be obtained by processes known from the literature (for example: W. N. Emmerling, B. Pfannemüller, Starch 33 (6), 202 (1981); R. Schaffer; H. S. Isbell, J. Am. Chem. Soc. 81, 2178 (1959), H. W. Diehl et al., Carbohydrate Research 38, 364 (1974)) by electrochemical or hypohalite oxidation of the corresponding aldoses.

To prepare the present bis-aldonamides, 2 moles of aldonolactone are employed per mole of diamino compound.

Suitable solvents for the reaction are methanol, ethanol, ethylene glycol, dimethyl sulfoxide, dimethyl-formamide or N-methylpyrrolidone. Dimethylformamide is preferred.

The reaction times are several hours to days, preferably between 5 and 8 hours.

The reaction temperatures are between room temperature and the boiling temperatures of the respective solvent, preferably between 40° C. and 80° C.

The aldonamides either crystallize out from the reaction solution or can be precipitated by addition of an organic solvent. Suitable for this are methanol, ethanol, isopropanol or acetone, preferably isopropanol.

In a preferred embodiment of the process according to the invention, the compounds of the formula I are produced from the aldonic acids of the formula X without isolation of the lactones.

In this connection, an aqueous solution of the free aldonic acids X is prepared by means of a cation exchanger from alkali metal salts or alkaline earth metal salts of the aldonic acids X which can be purchased or synthesized by processes known from the literature (see above) and this is concentrated substantially. The lactones corresponding to the aldonic acids X are then produced without isolation by elimination of water. For this purpose, the residue, which represents a water-containing mixture of aldonic acid and lactone, is dissolved in a high-boiling solvent. Examples of high-boiling solvents are dimethyl sulfoxide, dimethylformamide, N-methylpyrrolidone, dimethoxymethyl ether etc., dimethylformamide being preferred. A second, low-boiling solvent which can form an azeotrope with water is then added. Suitable solvents are, for example, n-pentane, n-hexane, cyclohexane, benzene etc., n-hexane being preferred. Water is then eliminated quantitatively from the aldonic acids in a water separator. The low-boiling solvent is then distilled off and the lactone situated in the remaining, high-boiling solvent is reacted, without isolation of same, with the diamino compound. The reaction temperatures are between 20° C. and 120° C., preferably between 50° C. and 80° C. The reaction products are obtained by precipitating with an organic solvent. Suitable solvents are, for example, diethyl ether and other ethers, methanol, ethanol, isopropanol, carboxylic acid esters and acetone. Isopropanol and acetone are preferred. If necessary, the compounds can be freed from unreacted starting compounds by treating with acid and basic ion exchangers.

The further processing of the present bis-aldonamides to their polysulfated products and also these products themselves including their pharmacological properties are described in German Patent Application P 3734815.9 by the same Applicant of the same application date (case PSE-BAA, title: "Polysulfuric acid esters of bis-aldonamides and their derivatives, process for their preparation and medicaments"), whose disclosure shall presently be embraced in addition by way of reference.

The examples below illustrate the preparation of the present compounds and their further processing.

EXAMPLE 1

N,N'-1,3-propanediylbis-D-gluconamide 7.13 g of D(+)-glucono-1,5-lactone are dissolved in 40 ml of amine-free dimethylformamide and 1.67 ml of 1,3-diaminopropane are added. The mixture is then warmed to 60° C. and stirred for 5 hours. The resulting precipitate is filtered off, washed with methanol and dried. 7.96 g of a white powder are obtained.

Melting point: 165°–173° C.

IR (KBr): ν=3540, 2960, 2915, 2890, 1660, 1537, 1100, 1040 cm$^{-1}$ $^1$H-NMR (D$_2$O): δ 1.76 (dt, 2H, 6.5 Hz); 3.30 (t, 4H, 6.5Hz); 3.4–4.0 (m, 8H); 4.09 (m, 2H); 4.30 (d, 2H, 3 Hz); 4.70 (H$_2$O, int. std.)

EXAMPLE 2

N,N'-1,12-dodecanediylbis-D-gluconamide 7.1 g of D-glucono-1,5-lactone are suspended in 90 ml of dimethylformamide, 4.0 g of 1,12-diaminododecane are added and the mixture is stirred for 5 hours at 60° C. After cooling, the mixture is stirred into 0.3 liters of methanol, and the solid is collected and washed with methanol. The solid is then suspended in 1 N HCl, stirred for 1 hour at room temperature, and the solid is collected again and washed with water, acetone and finally with diethyl ether. 9.9 g of a white powder are obtained.

Melting point: 192°–195° C.

IR (KBr): ν=2920, 2850, 1630, 1550, 1085, 1027 cm$^{-1}$ $^1$H-NMR (DMSO-d$_6$): δ 0.7–1.8 (m, 20H); 3.06 (m, 4H); 3.25–3.75 (m, 8H); 3.75–4.2 (m, 4H); 4.40 (S, 10H); 7.51 (t, 2H, 5.5 Hz); int. std.: tetramethylsilane

EXAMPLE 3

N,N'-1,3-propanediylbis[4-O-β-D-galactopyranosyl-D-gluconamide]

395.4 g of calcium lactobionate are dissolved in 1.2 liters of water and the solution is treated for 1 hour with 0.7 liters of Lewatit S 100 (H$^+$ form) in a batch process. The mixture is filtered with suction and the exchanger is washed with 2×1 liter of water. The combined eluates are concentrated substantially in vacuo. The glass-like residue is then dissolved in 800 ml of amine-free dimethylformamide, 800 ml of n-hexane are added and the mixture is heated to boiling in a water separator with vigorous stirring. After water separation is complete, the n-hexane is distilled off, 43 ml of 1,3-diaminopropane are added and the mixture is stirred for 7 hours at 63° C. The mixture is then stirred into 5 liters of isopropanol, and the solid is collected and washed with 1 liter of isopropanol. After drying, 350 g of a white solid are obtained. For purification, this is dissolved in 2 liters of water. The solution is treated for 1 hour with 100 ml of Lewatit S 100 (H$^+$ form), then with 100 ml of Amberlyst A 21 (OH$^-$ form). After freeze-drying, the title compound is obtained in pure form.

Melting point: 125°–132° C.

IR (KBr): ν=2930, 1645, 1550, 1080 cm$^{-1}$ $^1$H-NMR (D$_2$O): δ 1.75 (d, 2H, 6HZ); 3.27 (t, 4H, 6 Hz); 3.4–4.1 (m, 20H); 4.15 (t, 2H, 3 Hz); 4.39 (d, 2H, 3 Hz); 4.54 (d, 2H, 7 Hz); 4.70 (H$_2$O, int. std.)

$^{13}$C-NMR (D$_2$O): δ 30.79; 38.99; 63.73; 64.65; 71.30; 73.12; 73.74; 74.14; 74.50; 75.06; 75.18; 77.99; 83.71; 106.10; 176.84 int. std.: CH$_3$OH δ 51.56

EXAMPLE 4

N,N'-1,6-hexanediylbis[4-O-β-D-galactopyranosyl-D-gluconamide]

17.0 g of lactobiono-1,5-lactone are suspended in 100 ml of amine-free dimethylformamide, 2.9 g of 1,6-diaminohexane are added and the mixture is stirred for 6 hours at 80° C. After cooling, the mixture is filtered and the filtrate is stirred into 1 liter of diethyl ether. The partly oily precipitate is dissolved in 50 ml of water and treated with 80 ml of ion exchanger (Merck 4765, H$^+$ form). The mixture is filtered and, after lyophilization, 19.5 g of colorless powder which decomposes from 175° C. with brown coloration are obtained.

IR: ν=2930, 2860, 1645, 1548, 1080 cm$^{-1}$ $^1$H-NMR (D$_2$O): δ 1.0–1.8 (m, 8H); 3.25 (t, 4H, 5.5 Hz); 3.3–4.1 (m, 20H); 4.15 (t, 2H, 3 Hz); 4.38 (d, 2H, 3 Hz); 4.55 (d, 2H, 7 Hz); 4.70 (H$_2$O) int. std.: 3-trimethylsilylpropanesulfonic acid Na salt $^{13}$C-NMR (D$_2$O): δ 28.19; 30.89; 41.63; 63.68; 64.64; 71.25; 73.06; 73.72; 74.12; 74.96; 75.18; 77.97; 83.61; 106.08; 176.42 int. std.: CH$_3$OH δ 51.54

EXAMPLE 5

N,N'-1,12-Dodecanediylbis[4-O-β-D-galactopyranosyl-D-gluconamide]

40.8 g of lactobiono-1,5-lactone are suspended in 150 ml of amine-free dimethylformamide, 12.0 g of 1,12-diaminododecane are added and the mixture is stirred for 6 hours at 60° C. The mixture is added dropwise with stirring into 1.5 liters of isopropanol. The precipitate is washed with isopropanol and dissolved in 250 ml of water. The solution is treated first with 20 ml of an acid ion exchanger (Lewatit S 100), then with a basic ion exchanger (Merck 4767). After lyophilization, 35.0 g of a colorless powder are obtained.

Melting point: 79°–81° C.

IR: ν=2920, 2850, 1645, 1550, 1080 cm$^{-1}$ $^1$H-NMR (D$_2$O): δ 0.8–1.9 (m, 20H); 3.24 (t, 4H, 5.5 Hz); 3.4–4.1 (m, 20H); 4.17 (t, 2H, 3 Hz); 4.38 (d, 2H, 3 Hz); 4.55 (d, 2H, 7 Hz); 4.68 (H$_2$0, int. std.)

$^{13}$C-NMR (D$_2$O): δ 29.02; 31.36; 31.70; 41.86; 63.64; 64.69; 71.20; 73.08; 73.72; 74.17; 75.03; 75,20; 77.97; 83.72; 106.12; 176.24; int. std. CH$_3$OH δ 51.56

EXAMPLE 6

N,N'-1,9-Nonanediylbis[4-O-β-D-galactopyranosyl-D-gluconamide]

Preparation and purification are analogous to Example 5. 15.0 g of the title compound are obtained from 15.0 g of lactobiono-1,5-lactone and 3.47 g of 1,9-diaminononane.

IR: ν=2930, 2860, 1660, 1545, 1080 cm$^{-1}$ $^1$H-NMR (D$_2$O): δ 0.9–1.8 (m, 14H); 3.20 (t, 4H, 5.5 Hz); 3.3–4.1 (m, 20H); 4.15 (t, 2H, 3 Hz); 4.38 (d, 2H, 3 Hz); 4.55 (d, 7 Hz); 4.68 (H$_2$O, int. std.)

EXAMPLE 7

N,N'-1,12-Dodecanediylbis(4-O-β-D-glucopyranosyl-D-gluconamide)

2.04 g of cellobiono-1,5-lactone (H. W. Diehl et al., Carbohydr. Res. 38, 364 (1974)) are reacted with 0.60 g of 1,12-diaminododecane analogously to Example 5 and 0.60 g of the title compound are obtained.

IR: ν=2925, 2850, 1645, 1545, 1075, 1040 cm$^{-1}$ $^1$H-NMR (D$_2$O): δ 0.7–1.9 (m, 20H); 3.0–4.6 (m, 30H); 4.68 (H$_2$O int. std.)

EXAMPLE 8

N,N'-1,12-Dodecanediylbis(4-O-α-D-glucopyranosyl-D-gluconamide)

20.0 g of calcium maltobionate (W. N. Emmerling, B. Pfannemüller, Starch 33, 202, (1981)) are reacted with 1,12-diaminododecane analogously to Example 3 and 17.8 g of product are obtained.

IR: ν=2925, 2850, 1650, 1545, 1145, 1075, 1030 cm$^{-1}$
$^1$H-NMR (D$_2$O): δ 0.7–1.9 (m, 20H); 3.20 (t, 4H, 5.5 Hz); 3.3–4.4 (m, 24H); 5.15 (d, 2H, 3 Hz); 4.68 (H20, int. std)

EXAMPLE 9

N,N'-1,12-Dodecanediylbis(6-O-α-D-galactopyranosyl-D-gluconamide)

3.96 g of potassium melibionate (Sigma Chemie) are reacted with 1.00 g of 1,12-diaminododecane analogously to Example 3 and 3.3 g of the title compound are obtained.

Melting point: 114°–123° C.
IR (KBr): ν=2925, 1855, 1645, 1550, 1150, 1080, 1030, 980 cm$^{-1}$
$^1$H-NMR (D$_2$O): δ 0.8–1.8 (m, 20H); 3.20 (m, 4H); 3.4–4.2 (m, 22H), 4.29 (d, 2H, 3 Hz); 4.95 (s, 2H); 4.68 (H20, int. std)

EXAMPLE 10

N,N'-1,3-Propanediylbis(6-O-α-D-galactopyranosyl-D-gluconamide)

Preparation is analogous to Example 9. 3.0 g of product are obtained from 3.96 g of potassium melibionate and 0.37 g of 1,3-diaminopropane.

Melting point: 90°–96° C.
IR (KBr): ν=2925, 1645, 1550, 1152, 1080, 1030, 975 cm$^{-1}$
$^1$H-NMR (D$_2$O): δ 1.76 (dl.2H, 6.5 Hz); 3.30 (t, 4H, 6.5 Hz); 3.4–4.2 (m, 22H); 4.33 (d, 2H, 3 Hz); 4.96 (s, 2H); 4.70 (H20, int. std.)
$^{13}$C-NMR (D$_2$O): 30.73; 38.96; 63.75; 70.94; 74.13; 71.90; 72.12; 73.06; 73.52; 74.52; 75.97; 100.99; 176.91

EXAMPLE 11

N,N'-α,α'-m-Xylenediylbis[4-O-β-D-galactopyranosyl-D-gluconamide]

If 17.0 g of lactobiono-1,5-lactone and 3.3 ml of 3-(aminomethyl)benzylamine are used in a process according to Example 5, then 12.2 g of the title compound are obtained in the same way as a colorless powder.

IR: ν=2920, 1665, 1545, 1080 cm$^{-1}$
$^1$H-NMR (D$_2$O): δ 3.3–4.6 (m, 30H); 4.68 (H$_2$O); 7.24 (m, 4H)

EXAMPLE 12

N,N'-4,4'-Dicyclohexylmethanediylbis[4-O-β-D-galactopyraposyl-D-gluconamide]

Preparation and purification from 17.0 g of lactobiono-1,5-lactone and 5.3 g of 4,4'-diaminodicyclohexylmethane are analogous to Example 5.

Yield: 21.3 g.
IR: ν=2930, 2850, 1645, 1545, 1080 cm$^{-1}$
$^1$H-NMR (D$_2$O): δ 0.6–2.2 (m, 20H); 3.2–4.6 (m, 28H) 4.68 (H$_2$)

EXAMPLE 13

N,N'-1,6-(3,4-Dithiahexanediylbis)4-O-β-D-galactopyranosyl-D-gluconamide 6.9 ml of triethylamine are added at room temperature to 17.0 g of lactobiono-1,5-lactone and 5.63 g of cystamine dihydrochloride in 50 ml of amine-free DMF and the mixture is subsequently stirred for 6 hours at 60° C. It is then precipitated using 500 ml of ethanol and the precipitate is further treated as in Example 5. 13.2 g of white powder are obtained.

IR: ν=2925, 1650, 1545, 1080 cm$^{-1}$
$^1$H-NMR (D$_2$O): δ 2.90 (t, 4H, 6 Hz); 3.2–4.1 (m, 24H); 4.16 (t, 2H, 3 Hz); 4.38 (d, 2H, 3 Hz); 4.55 (d, 2H, 7 Hz), 4.68 (H20, int. std.)

EXAMPLE 14

N,N'-1,7-(4-Azaheptanediylbis)4-O-β-D-galactopyranosyl-D-gluconamide 17.0 g of lactobiono-1,5-lactone are suspended in 100 ml of amine-free dimethylformamide, 2.28 ml of bis-(3-aminopropyl)amine are added at room temperature and the mixture is stirred for 10 hours. It is then stirred for 4 hours at 40° C. and filtered. The filtrate is stirred into 900 ml of acetone and 23.0 g of white crystals are obtained after washing with acetone and drying. These are dissolved in 80 ml of water and precipitated using 900 ml of acetone. The partly oily precipitate is dissolved in 150 ml of water, filtered and lyophilized. Yield: 16.5 g.

IR: ν=2920, 1650, 1545, 1080 cm$^{-1}$
$^1$H-NMR (D$_2$O): δ 1.82 (d, 4H, 6 Hz); 2.91 (t, 4H, 6 Hz); 3.30 (t, 4H, 6 Hz); 3.45–4.6 (m, 26H); 4.68 (H$_2$O)

EXAMPLE 15

N,N'-1,12-(4,9-Dioxadodecanediylbis)-4-O-β-D-galactopyranosyl-D-gluconamide

Preparation and purification are analogous to Example 5. 18.9 g of the title compound are obtained from 17.0 g of lactobiono-1,5-lactone and 5.1 g of 1,12-diamino-4,9-dioxadodecane.

$^1$H-NMR: δ 1.4–2.0 (m, 8H); 3.1–4.1 (m, 32H); 4.6 (t, 2H, 3 Hz); 4.38 (d, 2H, 3 Hz); 4.55 (d, 2H, 7 Hz)

EXAMPLE 16

N,N'-Dimethyl-N,N'-1,2-ethanediylbis-(4-O-β-D-galactopyranosyl-D-gluconamide)

Preparation and purification are analogous to Example 5. 3.0 g of the title compound are obtained from 3.40 g of lactobiono-1,5-lactone and 0.44 g of N,N'-dimethylethylenediamine.

Melting point: 125°–133° C.
IR (KBr): ν=2930, 1640, 1400, 1075 cm$^{-1}$
$^1$H-NMR (D$_2$O): δ 2.99, 3.16 (2S, 6H); 3.3–4.3 (m, 28H); 4.49 (d, 2H, 7 Hz); 4.68 (H$_2$O, int. std.)

EXAMPLE 17

N,N'-1,5-(1-Ethoxycarbonyl)pentanediylbis-(4-O-β-D-galactopyranosyl-D-gluconamide)

2.47 g of lysine ethyl ester dihydrochloride are suspended in 40 ml of amine-free dimethylformamide, 3.0 ml of triethylamine are added and the mixture is stirred for 15 minutes. 6.8 g of lactobiono-1,5-lactone are then added, and the mixture is warmed to 60° C. and stirred for 1 day. It is then filtered and the filtrate is stirred into 400 ml of isopropanol. The precipitate is collected, dissolved in 60 ml of dimethylformamide and precipitated again using 300 ml of isopropanol. The precipitation is repeated, the precipitate is washed with isopropanol and diethyl ether and 4.05 g of a white powder are thus obtained.

Melting point: 106° C.
IR: ν=2930, 1735, 1655, 1550, 1075 cm$^{-1}$
$^1$H-NMR (D$_2$O): δ 1.25 (t, 3H, 7 Hz); 1.2–2.2 (m, 6H); 3.25 (t, 2H, 5.5 Hz); 3.4–4.6 (m, 29H); 4.68 (H$_2$O, int. std.)

EXAMPLE 18

Decasodium
N,N'-1,3-propanediylbis(2,3,4,5,6-penta-O-sulfo-D-gluconamide)

4.30 g of N,N'-1,3-propanediylbis-D-gluconamide are suspended in 50 ml of dry dimethylformamide and warmed to 40° C., and 23.9 g of pyridine-sulfur trioxide complex are added with stirring. After a few minutes, the product precipitates out in the form of the pyridinium salt as an oil. After 1 hour, the mixture is allowed to cool and the supernatant solution is decanted off. The oil is dissolved in 50 ml of water and brought to pH=10 using 6 N sodium hydroxide solution. The solution is made up to 90 ml using water and stirred into 350 ml of a 1% strength sodium acetate solution. The precipitate is washed with methanol and dried. 18.6 g of a colorless powder are obtained. This is dissolved in 186 ml of water. 227 ml of methanol are stirred into the solution and it is allowed to stand for 15 hours. The supernatant is decanted from the deposited oil and the latter is triturated with methanol. The precipitation is repeated until the title compound is pure.

Decomposition from 190° C. with brown coloration.

IR (KBr): ν=2960, 1670, 1555, 1250, 1073, 1045, 1019, 770 cm$^{-1}$ $^1$H-NMR (D$_2$O): δ 1.87 (dt, 2H, 7 Hz); 3.36 (dt, 4H, 7 Hz); 3.9–4.6 (m, 4H); 4.8–5.4 (m, 8H); 4.68 (H$_2$O), int. std.)

$[\alpha]_{20}^D = +26.2$ (c=5 in H$_2$O)

Elemental analysis: calc.: N 22.10%, S 1.93%, found: N 22.29%, S 1.83%.

$^{13}$C-NMR (D$_2$O): δ 29.97; 39.69; 69.06; 77.68; 78.10; 78.39; 79.65; 171.33; int. std.: CH$_3$OH δ 51.56

EXAMPLE 19

Decasodium
N,N'-1,12-dodecanediylbis-(2,3,4,5,6-penta-D-sulfo-D-gluconamide)

5.60 g of N,N'-1,12-dodecanediylbis-D-gluconamide are reacted with 25.5 g of pyridine-sulfur trioxide complex analogously to Example 18 and 20.5 g of crude product are obtained. The pure product is obtained by gel chromatography of an aqueous solution on a Sephadex G 25 column. After freeze-drying, a colorless powder which decomposes between 175° C. and 189° C. with brown coloration is obtained.

IR (KBr): ν=2930, 2855, 1665, 1555, 1250, 1072, 1042, 1010 cm$^{-1}$ $^1$H-NMR (D$_2$O): δ 1.0–1.9 (m, 20H); 3.32 (m, 4H); 4.2–4.6 (m, 4H); 4.9–5.3 (m, 8H); 4.68 (H$_2$O, int. std.)

$^{13}$C-NMR (D$_2$O): δ 28.72; 30.52; 31.02; 42.30; 69.22; 77.67; 78.34; 78.65; 79.91; 171.09; int. std. CH$_3$OH δ 51.56

EXAMPLE 20

Hexadecasodium
N,N'-1,3-propanediylbis[2,3,5,6-tetra-O-sulfo-4-O-(2,3,4,6-tetra-O-sulfo-β-D-galactopyranosyl)-D-gluconamide]

79.1 g of calcium lactobionate are dissolved in 240 ml of water and the solution is treated with 240 ml of Lewatit S 100 (H$^+$ form). The ion exchanger is washed using 3×200 ml of water and the combined solutions are concentrated as far as possible. The glass-like residue is dissolved in 700 ml of amine-free dimethylformamide and heated to boiling with 600 ml of n-hexane in a water separator. After water separation is complete, the n-hexane is evaporated off and 7.7 g of 1,3-diaminopropane in 50 ml of dimethylformamide are added to the solution at room temperature. After stirring for 5 hours at 60° C., the mixture is allowed to cool to about 30° C. and diluted with 450 ml of dimethylformamide, and 400 g of pyridinesulfur trioxide complex are added rapidly in portions with stirring. The mixture is stirred for 1 hour between 40° and 45° C. and allowed to cool. The supernatant is decanted from the deposited oil, and this is dissolved in 500 ml of water and the solution is adjusted to pH=10 using 30% strength sodium hydroxide solution. The solution is made up with water to a volume of 1.5 liters and stirred into 4.5 liters of a 1% strength methanolic sodium acetate solution. The precipitate is stirred with 1 liter of methanol, filtered off with suction and dried. 250 g of a yellowish powder are obtained. This is dissolved in 2 liters of water, 250 ml of 30% strength hydrogen peroxide are added and the mixture is stirred for 1 hour at 45° C. After cooling, it is neutralized and made up to 2.5 liters using water. The solution is stirred into 3.06 liters of methanol and allowed to stand for 15 hours. The supernatant is decanted from deposited oil and the latter is triturated with methanol. After drying, 188.5 g of colorless powder are obtained. The precipitation procedure is repeated four times and about 50 g of the pure title compound are finally obtained as a colorless powder which turns brown from 172° C. with decomposition and does not melt under 250° C.

IR (KBr): ν=2965, 1665, 1552, 1250, 1055, 1020, 927, 820 cm$^{-1}$ $^1$H-NMR (D$_2$O): δ 1.82 (t, 2H, 6.5 Hz); 3.35 (t, 4H, 6.5 Hz); 3.9–4.4 (m, 8H); 4.4–4.8 (m, +H$_2$O signal at 4.68 as int. std.); 4.8–5.4 (m, 10H)

$^{13}$C-NMR (D$_2$O): 30.31; 39.77; 68.36; 68.92; 74.22; 77.49; 77.79; 78.39; 78.76; 80.15; 103.55; 171.76; int. std.: CH$_3$OH δ 51.56

$[\alpha]_{20}^D = +13.3°$ (c=5 in H$_2$O)

Elemental analysis: calc.: N: 1.17%, S: 21.49%, found: N: 1.16%, S: 21.61%.

EXAMPLE 21

Pentadecasodium
pentadeca-O-sulfo-N,N'-1,3-propanediylbis(4-0-8-D-galactopyranosyl-D-gluconamide)

3.77 g of N,N'-1,3-propanediylbis(4-O-β-D-galactopyranosyl-D-gluconamide) are dissolved in 60 ml of dry dimethylformamide and 13.5 g of pyridine-sulfur trioxide complex are added in portions at 40° C. with stirring. After 1 hour, the mixture is worked up as in Example 18 and 10.3 g of yellowish, sulfate-containing crude product are obtained. This is dissolved in 90 ml of water, 10 ml of 30% strength hydrogen peroxide are added and the mixture is stirred for 1 hour at 45° C. After cooling, 230 ml of methanol are stirred in and the mixture is allowed to stand for 15 hours. The supernatant is decanted off from the deposited oil, the latter is triturated using methanol and 6.72 g of sulfate-free product (having a sulfur content of 20.6%) are obtained. This is dissolved in 67 ml of water, 82 ml of methanol are stirred in and the mixture is allowed to stand for 15 hours. The supernatant is decanted from the deposited oil and a further 74 ml of methanol are stirred in. After 15 hours, the oil is isolated and the fractional crystallization is repeated with it several times as above until the title compound is pure. 0.53 g of colorless powder which decomposes from 180° C. with brown coloration is obtained.

IR (KBr): ν=2960, 1660, 1550, 1250, 1055, 1020, 930, 820 cm$^{-1}$ $^1$H-NMR (D$_2$O): δ 1.87 (t, 2H, 6 Hz); 3.42 (t, 4H, 6 Hz); 3.9–4.5 (m, 8H); 4.5–4.85 (m + H$_2$O signal at 4.68 as int. std.); 4.85–5.3 (m, 10H)

$^{13}$C-NMR (D$_2$O): δ 30.53; 39.79; 68.46; 69.11; 72.28; 74.36; 74.56; 77.43; 77.88; 78.14; 78.49; 79.03; 79.61; 79.84; 80.43; 103.45; 171.82; 172.61; int. std.: CH$_3$OH δ 51.56

Elemental analysis: calc.: N 1.23%, S 21.04%, found: N 1.21%, S 20.91%.

EXAMPLE 22

Hexadecamorpholinium
N,N'-1,3-propanediylbis[2,3,5,6-tetra-O-sulfo-4-O-(2,3,4,6-tetra-O-sulfo-β-D-galactopyranosyl)-D-gluconamide]

A solution of 1.76 g of the sodium salt from Example 20 is treated for 15 minutes with 16 ml of Lewatit S-100 (H$^+$ form), the ion exchanger is filtered off and 1.03 g of morpholine are added to the filtrate. After lyophilization, 2.40 g of yellowish powder are obtained. Decomposition from 120° C. and black coloration at 210° C.

IR (KBr): ν=2950, 2780, 1665, 1563, 1450, 1426, 1250, 1097, 1015, 925, 893, 868, 810 cm$^{-1}$ $^1$H-NMR (D$_2$O): δ 1.82 (dt,2H; 6.5 Hz); 3.15 (m, 64H); 3.35 (m, 4H); 3.90 (m, 64H); 4.0–4.4 (m, 8H); 4.4–4.8 (m, +H$_2$0 signal at 4.70 as int. std.); 4.8–5.4 (m, 10H)

EXAMPLE 23

Hexadecasodium
N,N'-1,6-hexanediylbis[2,3,5,6-tetra-O-sulfo-4-O-(2,3,4,6-tetra-O-sulfo-8-D-galactopyranosyl)-D-gluconamide]

16.3 g of N,N'-1,6-hexanediylbis(4-O-β-D-galactopyranosyl-D-gluconamide) are reacted with 75.0 g of pyridine-sulfur trioxide complex analogously to Example 18. After the first precipitation, 56.9 g of a yellowish powder are obtained which is purified as in Example 20. About 15 g of the pure title compound are finally obtained in the form of a colorless powder which sinters from 120° C.

Decomposition from 170° C. with brown coloration.

IR (KBr): ν=2930, 2860, 1655, 1550, 1250, 1055, 1020, 928, 810 cm$^{-1}$ $^1$H-NMR (D$_2$O): δ 1.1–1.9 (m, 8H); 3.37 (m, 4H); 3.9–4.5 (m, 8H); 4.5–4.85 (m+H$_2$O signal at 4.68 as int. std.); 4.85–5.3 (m, 10H)

$^{13}$C-NMR (D$_2$O): δ 28.42; 30.74; 42.17; 68.56; 69.01; 74.39; 77.20; 77.80; 78.37; 78.94; 80.47; 103.21; 171.27; int. std. CH$_3$OH δ 51.56

$[α]_{20}^D$ = +9.9 (c=5 in H$_2$O)

EXAMPLE 24

Hexadecasodium
N,N'-1,9-nonanediylbis[2,3,5,6-tetra-O-sulfo-4-O-(2,3,4,6-tetra-O-sulfo-β-D-galactopyranosyl)-D-gluconamide]

Preparation and purification are analogous to Example 23. 45.0 g of crude product are obtained from 15.0 g of N,N'-1,9-nonanediylbis(4-O-β-D-galactopyranosyl-D-gluconamide) and 63.0 g of pyridine-sulfur trioxide complex. After purification: 10.5 g of colorless powder.

Decomposition between 192°–210° C. with brown coloration

IR (KBr): ν=2935, 2860, 1665, 1555, 1250, 1057, 1020, 925, 815 cm$^{-1}$ $^1$H-NMR (D$_2$O): δ 0.9–1.9 (m, 14H); 3.29 (t, 4H, 6.5 Hz); 3.8–4.45 (m, 8H); 4.45–4.8 (m+H$_2$O- signal at 4.68 as int. std.); 4.8–5.4 (m, 10H)

$^{13}$C-NMR (D$_2$O): δ 28.77; 30.83; 31.09; 31.32; 42.19; 68.69; 68.99; 74.46; 77.12; 77.79; 78.33; 78.93; 80.51; 103.11; 121.21 int. std.: CH$_3$OH, δ 51.56

EXAMPLE 25

Hexadecasodium
N,N'-1,12-dodecanediylbis[2,3,5,6-tetra-O-sulfo-4-O-(2,3,4,6-tetra-O-sulfo-β-D-galactopyranosyl)-D-gluconamide]

Preparation and purification are analogous to Example 23. 13.30 g of crude product are obtained from 4.23 g of N,N'-1,12-dodecanediylbis(4-O-β-D-galactopyranosyl-D-gluconamide) and 19.1 g of pyridine-sulfur trioxide complex. After purification: 3.5 g of pure title compound as colorless powder.

Decomposition between 188°–198° C. with brown coloration

IR (KBr): ν=2940, 2880, 1665, 1555, 1250, 1055, 1020, 930, 820 cm$^{-1}$ $^1$H-NMR (D$_2$O): δ 0.9–1.9 (m, 20H); 3.35 (t, 4H, 6.5 Hz); 3.9–4.5 (m, 8H); 4.5–4.8 (m, +H$_2$O signal at 4.70 as int. std.); 4.8–5.4 (m, 10H)

$^{13}$C-NMR (D$_2$O): δ 28.74; 30.80; 31.09; 31.44; 42.18; 68.76; 68.96; 74.50; 77.08; 77.80; 78.29; 78.94; 80.51; 103.07; 171.19 int. std.: CH$_3$OH δ 51.56

EXAMPLE 26

Hexadecasodium
N,N'-1,12-dodecanediylbis[2,3,5,6-tetra-O-sulfo-4-O-(2,3,4,6-tetra-O-sulfo-β-D-glucopyranosyl)-D-gluconamide]

0.68 g of crude or 0.10 g of pure product are obtained from 0.34 g of N,N'-1,12-dodecanediylbis(4-O-β-D-glucopyranosyl-D-gluconamide) and 1.12 g of pyridine-sulfur trioxide complex analogously to Example 23. Decomposition from 148° C. to 159° C. with brown coloration.

IR (KBr): ν=2930, 2855, 1670, 1560, 1250, 1070, 995, 935, 800 cm$^{-1}$ $^1$H-NMR (D$_2$O): δ 0.8–1.8 (m, 20H); 3.30 (m, 4H); 3.7–4.8 (m +H$_2$0 signal at 4.68 as int. std.); 4.8–5.3 (m, 10H)

$^{13}$C-NMR (D$_2$O): δ 28.92; 30.95; 31.32; 31.64; 42.34; 69.20; 70.12; 75.57; 77.44; 77.67; 77.85; 79.33; 79.41; 79.97; 81.08; 102.53; 171.27; int. std.: CH$_3$OH δ 51.56

EXAMPLE 27

Hexadecasodium
N,N'-1,12-dodecanediylbis[2,3,5,6-tetra-O-sulfo-4-O-(2,3,4,6-tetra-O-sulfo-α-D-glucopyranosyl)-D-gluconamide]

47.5 g of crude or 3.0 g of pure product are obtained from 12.8 g of N,N'-1,12-dodecanediylbis(4-O-α-D-glucopyranosyl-D-gluconamide) and 64.6 g of pyridine-sulfur trioxide complex analogously to Example 23. Decomposition from 175° C. to 189° C. with brown coloration.

IR (KBr): ν=2930, 2860, 1660, 1560, 1250, 1000, 943, 805 cm$^1$

¹H-NMR (D₂O): δ 1.0-1.9 (m, 20H); 3.27 (m, 4H); 4.0-4.82 (m+signal for H₂O at 4.68 as int. std.); 4.82-5.25 (m, 10H); 5.52 (d, 2H, 3 Hz)

¹³C-NMR (D₂O): δ 28.84; 30.69; 31.15; 31.47; 42.41; 68.51; 69.29; 71.95; 76.14; 76.82; 77.91; 78.30; 78.44; 79.98; 98.93; 171.27

EXAMPLE 28

Hexadecasodium
N,N'-1,12-dodecanediylbis[2,3,4,5-tetra-O-sulfo-6-O-(2,3,4,6-tetra-O-sulfo-o-D-galacto-pyranosyl)-D-gluconamide]

9.7 g of crude or 3.4 g of pure product, which sinters at 57° C., are obtained analogously to Example 23 from 3.30 g of N,N'-1,12-dodecanediylbis(6-O-α-D-galactopyranosyl-D-gluconamide) and 14.9 g of pyridine-sulfur trioxide complex.

Decomposition from 182° C. with brown coloration.
IR (KBr): ν=2930, 2855, 1650, 1555, 1250, 1050, 1027, 830 cm⁻¹

¹H-NMR (D₂O): δ 1.0-1.9 (m, 20H); 3.25 (m, 4H); 2.9-4.4 (m, 8H); 4.4-4.8 (m+H₂O signal at 4.68 as int. std.); 4.8-5.25 (m, 10H); 5.38 (d, 2H, 3 Hz)

¹³C-NMR (D₂O): δ 28.72; 30.58; 31.03; 31.34; 42.30; 69.14; 69.77; 70.66; 74.51; 74.92; 77.91; 78.21; 78.49; 78.93; 80.75; 99.12; 171.26; int. std.: CH₃OH δ 51.56

EXAMPLE 29

Hexadecasodium
N,N'-1,3-propanediylbis[2,3,4,5-tetra-O-sulfo-6-O-(2,3,4,6-tetra-O-sulfo-α-D-galactopyranosyl)-D-gluconamide]

0.96 g of crude or 0.50 g of pure product are obtained from 0.34 g of N,N'-1,3-propanediylbis(6-O-α-D-galactopyranosyl-D-gluconamide) and 2.0 g of pyridine-sulfur trioxide complex analogously to Example 23. Decomposition from 168° C. with brown coloration IR (KBr): ν=1640, 1550, 1250, 1050, 1025, 830 cm⁻¹

¹H-NMR (D₂O): δ 1.85 (t, 2H, 6.5 Hz); 3.35 (t, 4H, 6.5 Hz); 3.9-4.4 (m, 8H); 4.4-4.8 (m+H₂O signal at 4.68 as int. std.); 4.8-5.25 (m, 10H); 5.36 (d, 2H, 3 Hz)

¹³C-NMR (D₂O): δ 30.13; 39.84; 69.17; 69.86; 70.74; 74.53; 74.97; 78.00; 78.17; 78.37; 79.00; 80.81; 99.18; 171.70; int. std: CH₃OH δ 51,57

EXAMPLE 30

Hexadecasodium
N,N'-α,α'-m-xylenediylbis[2,3,5,6-tetra-)-sulfo-4-O-(2,3,4,6-tetra-O-sulfo-8-D-galactopyranosyl)-D-gluconamide]

28.0 g of crude or 5.3 g of pure product are obtained from 12.0 g of N,N'-α,α'-m-xylenediylbis(4-O-β-D-galactopyranosyl-D-gluconamide) and 58.8 g of pyridine-sulfur trioxide complex analogously to Example 23. Decomposition from 157° C. with brown coloration.

IR (KBr): ν=2960, 1660, 1550, 1250, 1055, 1020, 930, 815 cm⁻¹

¹H-NMR (D₂O): δ 3.9-4.85 (m+H₂O signal at 4.68 as int. std.), 4.85-5.4 (m, 10H); 7.38 (s, 4H)

¹³C-NMR (D₂O): δ 45.51; 68.63; 69.15; 74.42; 77.24; 77.67; 77.91; 78.49; 79.08; 80.70; 103.29; 128.15; 128.86; 131.64; 140.80; 171.88; int. std. CH₃OH δ 51.56

EXAMPLE 31

Hexadecasodium
N,N'-4,4'-dicylcohexylmethanediylbis[2,3,5,6-tetra-O-sulfo-4-O-(2,3,4,6-tetra-O-sulfo-β-D-galactopyranosyl)-D-gluconamide]

70.7 g of crude or 15.2 g of pure product, which sinters from 120° C., are obtained analogously to Example 23 from 25.7 g of N,N'-4,4'-dicyclohexylmethanediylbis(4-O-β-D-galactopyranosyl-D-gluconamide) and 114.7 g of pyridine-sulfur trioxide complex.

Decomposition from 180° C. with brown coloration.
IR (KBr): ν=2930, 2860, 1660, 1550, 1250, 1055, 1020, 928, 815 cm⁻¹

¹H-NMR (D₂O): δ 0.6-2.4 (m, 20H); 3.65 (m, 2H); 3.9-4.5 (m, 8H); 4.5-4.85 (m+H₂O signal at 4.68 as int. std.); 4.85-4.4 (m, 10H)

¹³C-NMR (D₂O): δ 30.18; 30.36; 30.75; 34.09; 44.40; 46.20; 49.45; 52.33; 68.27; 68.75; 74.35; 77.80; 78.41; 78.68; 79.49; 104.09; 170.61; int. std. CH₃OH δ 51.56
[α]₂₀ᴰ = +10.0 (c=5 in H₂O)

EXAMPLE 32

Hexadecasodium
N,N'-1,6-(3,4-dithiahexanediylbis)[2,3,5,6-tetra-O-sulfo-4-O-(2,3,4,6-tetra-O-sulfo-β-D-galactopyranosyl)-D-gluconamide]

38.0 g of crude and 8.5 g of pure product are obtained from 11.2 g of N,N'-1,6-(3,4-dithiahexanediylbis)4-O-β-D-galactopyranosyl-D-gluconamide and 53.4 g of pyridine-sulphur trioxide complex analogously to Example 23.

Decomposition from 163° C. with brown coloration.
IR (KBr): ν=2965, 1665, 1550, 1250, 1055, 1015, 930, 810 cm⁻¹

¹H-NMR (D₂O): δ 2.96 (t, 4H, 6.5 Hz); 3.69 (m, 4H); 4.0-4.47 (m, 8H); 4.45-4.8 (m+H₂O signal at 4.68 as int. std.); 4.8-5.3 (m, 10H)

¹³C-NMR (D₂O): δ 38.72; 41.06; 68.68; 69.05; 74.48; 77.40; 77.87; 78.46; 80.46; 103.48; 171.86; int. std. CH₃OH δ 4 51.56

EXAMPLE 33

Hexadecasodium
N,N'-1,7-(4-azaheptanediylbis)[2,3,5,6-tetra-O-sulfo-4-O-(2,3,4,6-tetra-O-sulfo-β-D-galactopyranosyl)-D-gluconamide]

15.4 g of crude and 2.2 g of pure product are obtained from 11.0 g of N,N'-1,7-(4-azaheptanediylbis)4-O-β-D-galactopyranosyl-D-gluconamide and 50.0 g of pyridine-sulfur trioxide complex analogously to Example 23.

Decomposition from 165° C. with brown coloration.
IR (KBr): ν=2960, 2925, 2855, 1650, 1550, 1250, 1055, 1020, 927, 820 cm⁻¹

¹H-NMR (D₂O): δ 2.98 (m, 2H); 3.17 (t, 4H, 7 Hz); 3.44 (t, 4H, 6 Hz); 3.9-4.4 (m, 8H); 4.4-4.85 (m +H20 signal as int. std. at 4.68); 4.85-5.3 (m, 10H)

¹³C-NMR (D₂O): δ 28.11; 39.08; 48 12; 68.65; 69.24; 74.45; 76.94; 77.93; 78.46; 79.09; 80.71; 103.13; 172.06

EXAMPLE 34

Hexadecasodium
N,N'-1,12-(4,9-dioxadodecanediylbis)[2,3,5,6-tetra-O-sulfo-4-O-(2,3,4,6-tetra-O-sulfo-β-D-galactopyranosyl)-D-gluconamide]

37.1 g of crude and 9.3 g of pure product, which sinters from 120° C., are obtained from 18.2 g of N,N'-1,12-(4,9-dioxadodecanediylbis)4-O-β-D-galactopyranosyl-D-gluconamide and 59.0 g of pyridine-sulfur trioxide complex according to Example 23.

Decomposition from 170° C. with brown coloration.

IR (KBr): ν=2960, 2880, 1665, 1555, 1250, 1055, 1022, 928, 815 cm$^{-1}$ $^1$H-NMR (D$_2$O): δ 1.64 (m, 4H); 1.88 (t, 4H, 6.5 Hz); 3.0–3.9 (m, 12H); 3.9–4.45 (m, 8H); 4.45–4.8 (m +H2O signal at 4.68 as int. std.); 4.8–5.3 (m, 10H)

$^{13}$C-NMR (D$_2$O): δ 27.82; 30.78, 39.02; 68.64; 69.01; 70.54; 72.96; 74.44; 77.02; 77.79; 78.33; 78.94; 80.52; 103.10; 171.45; int. std.: CH$_3$OH δ 51.56

[α]$_{20}^D$ = +9.0 (c=5 in H$_2$O)

EXAMPLE 35

Hexadecasodium
N,N'-dimethyl-N,N'-1,2-ethanediylbis[2,3,5,6-tetra-O-sulfo-4-O-(2,3,4,6-tetra-O-sulfo-β-D-galactopyranosyl)-D-gluconamide]

8.2 g of crude and 1.2 g of pure product are obtained from 2.50 g of N,N'-dimethyl-N,N'-1,2-ethanediylbis(4-O-β-D-galactopyranosyl-D-gluconamide) and 12.4 g of pyridine-sulfur trioxide complex analogously to Example 23.

Decomposition from 188°–200° C. with brown coloration.

IR (KBr): ν=2970, 1650, 1250, 1015, 930, 815 cm$^{-1}$ $^1$H-NMR (D$_2$O): δ 3.0–4.0 (m with s at 3.35; 10H); 4.0–4.7 (m, 14H); 4.70 (H$_2$O, int. std.); 4.9–5.4 (m, 10H); 5.54 (d, 2H, 4 Hz)

$^{13}$C-NMR (D$_2$O): δ 38.96; 48.28; 68.36; 69.25; 74.17; 75.11; 77.26; 77.73; 78.00; 78.45; 78.76; 79.80; 103.35; 171.25; int. std.: CH$_3$OH, δ 51.56

EXAMPLE 36

Hexadecasodium
N,N'-1,5-(1-ethoxycarbonyl)-pentanediylbis[2,3,5,6-tetra-O-sulfo-4-O-(2,3,4,6-tetra-O-sulfo-β-D-galactopyranosyl)-D-gluconamide]

8.7 g of crude and 1.2 g of pure product, which sinters from 60° C., are obtained from 3.6 g of N,N'-1,5-(1-ethoxycarbonyl)-pentanediylbis(4-O-β-D-galactopyranosyl-D-gluconamide) and 15.8 g of pyridine-sulfur trioxide complex according to Example 23.

Decomposition from 161° C. with brown coloration.

IR (KBr): ν=1730, 1650, 1550, 1250, 1055, 1020, 930, 810 cm$^{-1}$ $^1$H-NMR (D$_2$O): δ 1.0–2.2 (m, 9H, with t at 1.31, 7 Hz); 3.30 (m, 2H); 3.9–4.8 (m with H$_2$O signal at 4.68 as int. std.); 4.8–5.3 (m, 10H)

$^{13}$C-NMR (D$_2$O): δ 15.94; 29.68; 30.54; 33.17; 41.87; 55.93; 65.19; 68.23; 68.53; 69.04; 74.36; 77.33; 79.81; 78.45; 78.80; 79.61; 80.47; 103.36; 103.99; 171.39; 171.65; 176.12

EXAMPLE 37

N,N'-1,3-Propanediylbis-D-gulonamide 3.56 g of D-gulono-γ-lactone and 0.84 ml of 1,3-diaminopropane are dissolved in 40 ml of dimethylformamide and the mixture is stirred for 6 hours at 60° C. The mixture is then stirred into 200 ml of isopropanol and the precipitate is washed with isopropanol and diethyl ether. The solid is dissolved in 20 ml of dimethylformamide and precipitated again using 200 ml of isopropanol. The precipitate is dissolved in water and freeze-dried. 2.2 g of a colorless powder are obtained. Melting point: 49°–54° C. with sintering, 168° C. with decomposition IR (KBr): ν=2930, 2890, 1645, 1545, 1440, 1080 cm$^{-1}$ $^1$H-NMR (D$_2$O): δ 1.74 (dt,2H, 6.5 Hz); 3.27 (t, 4H, 6.5 Hz); 3.45–4.05 (m, 10H); 4.23 (d, 2H, 6 Hz); 4.68 (H$_2$O, int. std.)

$^{13}$C-NMR (D$_2$O): δ 30.65; 39.02; 65.13; 72.64; 74.69; 75.00; 75.12; 176.78; int. std. CH$_3$OH δ 51.56

EXAMPLE 38

N,N'-1,2-Propanediylbis-D-galactonamide 4.1 g of the title compound as colorless powder are obtained analogously to Example 37 from 7.12 g of D-galactono-γ-lactone and 1.48 g of 1,2-diaminopropane. Melting point: 183°–193° C. with decomposition and brown coloration IR (KBr): ν=2940, 1656, 1552, 1109, 1055, 1044, 1028, 865 cm$^{-1}$ $^1$H-NMR (D$_2$O): δ 1.18 (d, 3H, 6 Hz); 3.1–4.6 (m, 15H); 4.68 (H$_2$O, int. std.)

$^{13}$C-NMR (D$_2$O): δ 19.64; 19.77; 46.16; 47.87; 48.10; 65.90; 71.93; 72.64; 73.49; 177.75; 178.42; 178.54

EXAMPLE 39

N,N'-1,4-Butanediylbis-L-mannonamide 2.4 g of the title compound are obtained as colorless powder analogously to Example 18 from 3.56 g of L-mannono-γ-lactone and 0.90 g of potrescine.

Decomposition from 181°–188° C. with brown coloration

IR (KBr): ν=2955, 2925, 2855, 1643, 1555, 1231, 1098, 1043, 1031, 880, 740, 640 cm$^{-1}$ $^1$H-NMR (D$_2$O): δ 1.58 (m, 4H); 3.30 (m, 4H); 3.75 (m, 8H); 4.02 (d, 2H, 7 Hz); 4.26 (d, 2H, 7 Hz); 4.68 (H$_2$O int. std.)

$^{13}$C-NMR (D$_2$O): δ 28.42; 41.38; 65.67; 72.58; 72.76; 73.43; 75.19; 177.09

EXAMPLE 40

N,N'-Dilactobionoylhydrazine 6.1 g of crude product are obtained analogously to Example 37 from 6.8 g of lactobiono-1,5-lactone and 0.5 ml of hydrazine hydrate. Column chromatography over Fractogel TSK HW 40S yields the pure product as colorless powder after freeze-drying.

EXAMPLE 41

Decasodium
N,N'-1,3-propanediylbis(2,3,4,5,6-penta-O-sulfo-D-gulonamide)

9.8 g of crude or 6.4 g of pure product as colorless powder are obtained analogously to Example 18 from 2.2 g of N,N'-1,3-propanediylbis-D-gulonamide and 12.3 g of pyridine-sulfur trioxide complex.

Decomposition from 185° C. with brown coloration.

IR (KBr): ν=2960, 1675, 1555, 1250, 1070, 1010, 925, 805 cm$^{-1}$

¹H-NMR (D₂O): δ 1.85 (m, 2H); 3.34 (m, 4H); 4.52 (d, 4H, 3.5 Hz); 5.07 (m, 6H); 5.34 (d, 2H, 3.5 Hz); 4.68 (H20, int. std.)

¹³C-NMR (D₂O): δ 30.05; 39.62; 68.78; 76.28; 76.41; 77.78; 80.14; 171.15; int. std. CH₃OH δ 51.55

EXAMPLE 42

Decasodium N,N'-1,2-propanediylbis(2,3,4,5,6-penta-O-sulfo-D-galactonamide)

13.0 g of crude or 9.8 g of pure product as colorless powder are obtained analogously to Example 18 from 3.3 g of N,N'-1,2-propanediylbis-D-galactonamide and 19.5 g of pyridine-sulfur trioxide complex.

Decomposition from 191° C. with brown coloration.

IR (KBr): ν=2970, 1665, 1550, 1250, 1065, 1040, 1007, 900 cm⁻¹

¹H-NMR (D₂O): δ 1.26 (d, 3H, 6.5 Hz); 2.9–4.3 (m, 3H); 4.3–4.6 (m, 4H); 4.68 (H₂O, int. std.); 4.8–5.3 (m, 8H)

¹³C-NMR (D₂O): δ 19.20; 45.94; 46.15; 47.61; 69.07; 78.42; 78.86; 79.90; 170.84; 171.03; 191.93 int. std. CH₃OH δ 51.57

EXAMPLE 43

Decasodium N,N'-1,4-butanediylbis(2,3,4,5,6-penta-O-sulfo-L-mannonamide)

10.5 g of crude or 7.2 g of pure product as colorless powder are obtained analogously to Example 18 from 2.5 g of N,N'-1,4-butanediylbis-L-mannonamide and 14.1 g of pyridine-sulfur trioxide complex.

Decomposition from 180° C. with brown coloration

IR (KBr): ν=2960, 2930, 2850, 1670, 1555, 1250, 1075, 1010, 925 cm⁻¹

¹H-NMR (D₂O): δ 1.65 (m 4H); 3.31 (m, 4H), 4.43 (m, 4H); 4.8–5.08 (m, 4H); 5.15 (m, 4H); 4.68 (H₂O, int. std.)

¹³C-NMR (D₂O): δ 27.98; 41.62; 69.15; 78.81; 79.36; 79.75; 170.93; int. std. CH₃OH δ 51.55

EXAMPLE 44

Hexadecasodium N,N'-bis[2,3,5,6-tetra-O-sulfo-4-O-(2,3,4,6-tetra-O-sulfo-8-D-galactopyranosyl)gluconoyl]hydrazine 17.5 g of crude or 7.3 g of pure product are obtained analogously to Example 18 from 6.0 g of N,N'-dilactobionoylhydrazine and 33.7 g of pyridine-sulfur trioxide complex.

Example 45

5.000 kg of hexadecasodium N,N'-1,3-propanediylbis[2,3,5,6-tetra-O-sulfo-4-O-(2,3,4,6-tetra-O-sulfo-β-D-galactopyranosyl)-D-galactopyranosyl)-D-gluconamide] as dry substance are dissolved with stirring in 40 liters of water for injection. After adjusting the pH of the solution to 7.5 with dilute sodium hydroxide solution, it is made up to 50.00 liters with water for injection and filtered through a mebrane filter of pore size 0.2 μm. The solution is filtered off under aseptic conditions into ampoules of 1 ml and these are sealed off.

I claim:

1. Bis-aldonamides of the formula (I):

$$\left( R^1O-CH_2-CH(OH)-CH(OR^2)-CH(OR^3)- \right.$$

$$\left. -CH(OH)-\overset{O}{\underset{\|}{C}}-N(R^4)-\right)_2 A$$

in which either all radicals $R^1$, $R^2$ and $R^3$ represent a hydrogen atom, or two of the radicals $R^1$, $R^2$ and $R^3$ represent a hydrogen atom and the third represents a radical of the formulae (II) to (VII):

(II) [β-D-galactopyranosyl structure with CH₂OH, HO, OH groups]

(III) [α-D-galactopyranosyl structure with CH₂OH, HO, OH groups]

(IV) [β-D-mannopyranosyl structure with CH₂OH, HO, OH groups]

(V) [α-D-mannopyranosyl structure with CH₂OH, HO, OH groups]

(VI) [disaccharide structure with α-linkage, repeating unit m]

(VII) [disaccharide structure with β-linkage, repeating unit m]

wherein m is 0, 1, 2, 3, 4, 5 or 6,

A in formula (I) represents a straight-chain or branched, saturated alkylene radical having 2 to 22 carbon atoms which is unsubstituted or substituted by one or more radicals —CO₂R⁵ or A represents a single bond or the radical

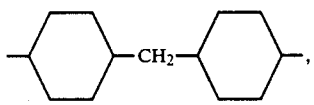

R$^4$ and R$^5$ independently represent a hydrogen atom or a C$_1$-C$_6$ alkyl radical, and their salts of inorganic or organic bases, with the proviso that in the case of bis-gluconic acid amides a) R$^1$, R$^2$, R$^4$ and R$^4$ do not identically represent hydrogen atoms and that b) when R$^2$ is a radical of the formula (II), and R$^1$, R$^3$ and R$^4$ are hydrogen atoms, A is not —(CH$_2$-)$_2$— and that c) when R$^2$ is a radical of the formula (VI), in which m=0, 1, 2, 3, or 5, and R$^1$, R$^3$ and R$^4$ are hydrogen atoms and A is an unsubstituted, straight-chain alkylene radical, the number of chain members is an uneven number.

2. Compounds as claimed in claim 1, wherein the saturated alkylene radical having 2 to 22 carbon atoms which is substituted or unsubstituted by one or more radicals —CO$_2$R$^5$ is interrupted by up to five —O—, —S—, —S—S—, —S(O)$_n$—,

and/or —NR$^6$— groups or cycloalkylene or arylene radicals, wherein R$^5$ and R$^6$ which may be identical or different represent a hydrogen atom or a C$_1$-C$_6$-alkyl radical and n is 1 or 2.

3. Compounds as claimed in claim 1 or 2, wherein R$^2$ and R$^3$ represent hydrogen atoms.

4. Compounds as claimed in claim 3, wherein R$^1$ represents the radical (III) or the radical (VI) and m=0.

5. Compounds as claimed in claim 3, wherein A in formula (I) represents a polymethylene radical —(CH$_2$-)$_p$— and p=2 to 12.

6. Compounds as claimed in claims 1 or 2, wherein R$^1$ and R$^3$ represent hydrogen atoms.

7. Compounds as claimed in claim 6, wherein R$^2$ represents the radical (II) or the radical (VI) and m=0 or the radical (VII) and m=0.

8. Compounds as claimed in claim 6, wherein A in formula (I) represents a polymethylene radical —(CH$_2$-)$_p$— and p=2 to 22.

9. Compounds as claimed in claim 8, wherein A in formula (I) represents a polymethylene radical —(CH$_2$-)$_p$— and p=2 to 12.

10. Compounds as claimed in claim 8, wherein A in formula (I) is substituted by one, two or more radicals of —CO$_2$R$^5$, where R$^5$ represents a hydrogen atom or a C$_1$-C$_6$-alkyl radical.

11. Compounds as claimed in claim 2, wherein A in formula (I) represents a straight-chain alkylene radical having 2 to 22 carbon atoms, whose chain can be interrupted by the groups —O—, —S—, —S—S—, —S-(O)$_n$—,

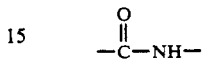

and/or —NR$^6$—, where n is 1 or 2, and R$^6$ represents a hydrogen or a C$_1$-C$_6$-alkyl radical.

12. A process for the preparation of bis-aldonamides of the formula (I) as claimed in claims 1 or 2, wherein an aldonolactone of the formulae (VIII) or (IX):

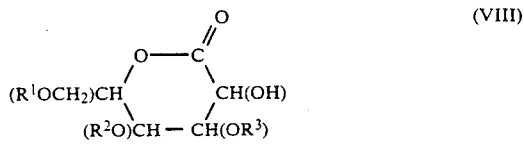

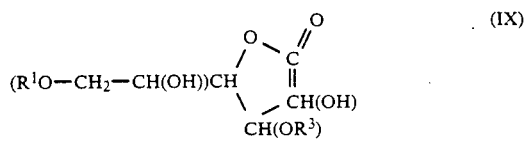

is reacted with a diamino compound of the formula R$^4$HN—A—NHR$^4$, in which R$^4$ represents a hydrogen atom or a C$_1$-C$_6$-alkyl radical and A is as indicated above.

13. The process as claimed in claim 12, wherein the aldonolactone of the formulae (VIII) and (IX) are prepared in situ by eliminating water from the corresponding aldonic acids of the formula (X)

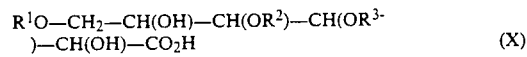

and are reacted with the diamino compound without isolation.

* * * * *